(12) United States Patent
Nakaya et al.

(10) Patent No.: US 6,537,828 B1
(45) Date of Patent: Mar. 25, 2003

(54) IMMUNOASSAY APPARATUS

(75) Inventors: Miho Nakaya; Ryotaro Chiba, both of Matsudo (JP)

(73) Assignee: Dainabot Co., Ltd., Tokyo (JP)

( * ) Notice: Subject to any disclaimer, the term of this patent is extended or adjusted under 35 U.S.C. 154(b) by 0 days.

(21) Appl. No.: 09/423,297

(22) PCT Filed: Jul. 27, 1998

(86) PCT No.: PCT/JP98/03334

§ 371 (c)(1),
(2), (4) Date: Dec. 13, 1999

(87) PCT Pub. No.: WO99/05526

PCT Pub. Date: Feb. 4, 1999

(30) Foreign Application Priority Data

Jul. 28, 1997 (JP) .............................................. 9-201888

(51) Int. Cl.[7] ............................................. G01N 33/558
(52) U.S. Cl. ......................... 436/514; 422/55; 422/56; 422/57; 422/58; 422/61; 435/287.1; 435/287.2; 435/287.7; 435/287.9; 435/805; 435/810; 435/970; 436/518; 436/530; 436/169; 436/805; 436/810
(58) Field of Search ............................... 422/55–58, 61; 435/287.1, 287.2, 287.7, 287.9, 805, 810, 970; 436/514, 518, 530, 169, 805, 810

(56) References Cited

U.S. PATENT DOCUMENTS

| | | | |
|---|---|---|---|
| 4,960,691 A | | 10/1990 | Gordon et al. |
| 5,384,264 A | * | 1/1995 | Chen et al. .................. 436/525 |
| 5,712,172 A | * | 1/1998 | Huang et al. ................ 436/518 |
| 5,965,458 A | * | 10/1999 | Kouvonen et al. .......... 436/518 |

FOREIGN PATENT DOCUMENTS

| | | |
|---|---|---|
| EP | 0 420 021 | 4/1991 |
| JP | 63-96559 | 4/1988 |
| JP | 01-503174 A | 10/1989 |
| JP | 09-504873 A | 5/1997 |
| WO | 88/08534 A1 | 4/1988 |
| WO | 92/08972 | 4/1992 |
| WO | 93/24231 | 12/1993 |
| WO | 95/13542 | 11/1994 |

* cited by examiner

*Primary Examiner*—Christopher L. Chin
(74) *Attorney, Agent, or Firm*—Oblon, Spivak, McClelland, Maier & Neustadt, P.C.

(57) ABSTRACT

An immunoassay device which comprises a Chromatography strip having a substrate adhered to the under surface thereof and a protective laminate adhered to the top surface thereof, wherein a space is arranged on the top and/or under surface of at least a partial region of a coloring region of the chromatography strip.

8 Claims, 4 Drawing Sheets

(A)

(B)

(A)

(B)

IMMUNOASSAY APPARATUS

FIELD OF THE INVENTION

This invention relates to an immunoassay device in which a chromatography strip is used. More particularly, it relates to an immunoassay device which comprises a chromatography strip having a substrate adhered to the under surface thereof and a protective laminate adhered to the top surface thereof, wherein a space is arranged on the top and/or under surface of at least a partial region of a coloring region of said chromatography strip.

PRIOR ART

As is well known, in an immunoassay device having a chromatography strip, a system is arranged so that an added sample solution to be tested can move in the chromatography strip by the force of capillary flow, and a detecting region of an analyte is arranged on a downstream part of a region where the sample solution is added. The detecting region is arranged in such a manner that it develops a color or its coloring degree is reduced when a sample solution arrived thereto contains an analyte, so that the presence or quantity of the analyte can be detected or measured based on the coloring degree of the detecting region. Such a type of immunoassay device has been described for example in JP-A-61-145459 (the term "JP-A" as used herein means an "unexamined published Japanese patent application"), JP-A-64-32169, JP-A-1-113662, JP-A-1-244370, J-PA-1-63865 and JP-W-1-503174 (the term "JP-W" as used herein means an "unexamined published Japanese international patent application"), and these descriptions are included herein as a part of the description of the present invention.

Each of these immunoassay devices has a chromatography strip in which a substrate is adhered to the under surface thereof and a protective laminate is adhered to the top surface thereof, in order to protect the chromatography strip and prevent biohazard.

According to a study conducted by the inventors of the present invention, it has been found that the capillary flow of sample solution is not uniform in a region of a chromatography strip where analytical reagents are immobilized such as a coloring region. When the flow of a sample solution is not uniform in a coloring region, development of color in the coloring region becomes so irregular that white spots and the like are formed in the coloring region, thus causing reduction of the detection accuracy.

As an attempt to unify capillary flow of a sample solution through a chromatography strip, a technique is disclosed in Patent Publication No. 2590055 in which both ends of a chromatography strip in its longitudinal direction are made into a continuous dentate (concave-convex) shape, but this is not an attempt to unify the flow in the coloring region.

PROBLEMS TO BE RESOLVED BY THE INVENTION

In consequence, the object of the present invention is to provide an immunoassay device in which a chromatography strip is used in such a manner that capillary flow of a sample solution in its coloring region becomes uniform.

MEANS FOR RESOLVING THE PROBLEMS

The inventors of the present invention have found that white spots and the like problems caused by irregular capillary flow in a coloring region do not occur and high detection accuracy can be obtained when a space is arranged in at least a partial region of the coloring region in a chromatography strip which has a substrate adhered to the under surface thereof and a protective laminate adhered to the top surface thereof. Accordingly, the present invention is an immunoassay device which comprises a chromatography strip having a substrate adhered to the under surface thereof and a protective laminate adhered to the top surface thereof, wherein a space is arranged on the top and/or under surface of at least a partial region of a coloring region of the chromatography strip.

MODE OF CARRYING OUT THE INVENTION

As shown in FIG. 1, the immunoassay device of the present invention has a chromatography strip (1) in which a substrate (2) is adhered to its under surface and a protective laminate (3) is adhered to its top surface.

As the chromatography carrier of the chromatography strip, any of those which are known in this field can be used. For example, cellulose, nitrocellulose, cellulose acetate and the like are used most frequently.

The substrate and protective laminate are adhered to the chromatography strip by applying a paste (4) to the substrate and protective laminate. For example, a rubber, acrylic, vinyl ether polymer or the like adhesive is used as the paste.

When nitrocellulose or the like carrier which is soluble in organic solvents is used as the chromatography carrier, the chromatography carrier and the substrate may be adhered by dissolving nitrocellulose in an organic solvent such as acetone or the like and spreading the solution on a substrate composed of polyethylene terephthalate or the like film which is soluble in the solvent or on a substrate having the same film. Such a case is also included in the adhering of the chromatography strip to the substrate of the present invention.

The substrate and protective laminate may be those which are usually used in the conventional immunoassay devices in which chromatography strips are employed. For example, polyethylene terephthalate, polypropylene, polyvinyl chloride and the like may be used.

The chromatography strip has a sample applying region (5), and when a sample solution having a possibility of containing an analyte is applied to the sample applying region, the sample solution moves to the downstream direction by the force of capillary flow.

The chromatography strip also has a coloring region at a downstream position of the sample applying region. The coloring region is a region which develops color during the assay, and it includes a detecting region (6) for detecting an analyte in a sample solution. As occasion demands, a control region (7) may be arranged as a coloring region.

The detecting region is arranged in such a manner that a tracer comprised of a labeled antigen or antibody is accumulated in response to the presence or quantity of an analyte contained in a sample solution which is migrated form the upstream area by the force of capillary flow. The term "in response to the presence or quantity of an analyte" as used herein means that the amount of accumulated tracer increases in the case of a sandwich assay or the amount of accumulated tracer decreases in the case of a competitive assay. That is, the detecting region contains an immobilized compound to which, if necessary via a certain crosslinking compound, an analyte specifically binds (in this case, a tracer binds specifically to the analyte also) or specifically binds in competition with the tracer.

The term "crosslinking compound" as used herein means a substance which binds specifically to both of the compound immobilized to the detecting region and an analyte. For example, there is a case in which an anti-mouse IgG antibody is immobilized to the detecting region and a mouse IgG for an analyte antigen is used as the crosslinking compound. Also, it is possible to use, as the crosslinking compound, a conjugate composed of a compound which specifically binds to the compound immobilized to the detecting region and a substance that specifically binds to an analyte. In this case, the substance that specifically binds to an analyte may be an antibody when the analyte is an antigen, or an antigen when the analyte is an antibody. The combination of a compound immobilized to the detecting region and a compound which specifically binds to the compound immobilized to the detecting region may be biotin as one and anti-biotin antibody or avidin as the other, or a saccharide as one and a saccharide-binding protein as the other.

When an analyte and a tracer competitively bind to the compound immobilized to the detecting region, a second detecting region may be arranged at a position downstream of the detecting region, in order to capture the tracer which has not been captured at the detecting region. This second detecting region is also included in the "detecting region" of the present invention.

Examples of the marker to be used include enzymes relating to coloring developing reactions, gold colloid and the like metal colloids, selenium colloid and the like non-metal colloids, and colored resin microparticles, colored liposomes, dyestuff microparticles and the like colored microparticles. In consequence, coloring degree of the detecting region changes when the tracer is accumulated or not accumulated in the detecting region, whereby the presence or quantity of an analyte in a sample solution can be known by measuring the coloring degree with the naked eye or using an instrument.

The control region is a region which is employed to know if a sample solution has properly passed through the detecting region, and is arranged, when required, in such a manner that the control region develops a color when the sample solution reaches the control region. The control region is arranged at a position downstream of the detecting region as occasion demands. Development of color when a sample solution reaches the control region can be effected by a well known method, for example by including a pH indicator, an enzyme which takes charge of the coloring reaction or a tracer in the sample solution and immobilizing a compound to the control region which develops a color when such a substance reaches the region.

The tracer may be included in advance in a specified region (labeling region (8)) of the chromatography strip or added together with a sample solution when the sample solution is applied.

The term "top surface" as used herein means the side of chromatography strip which the protective laminate is adhered to, and the term "under surface" means the side of chromatography strip which the substrate is adhered to.

The term "space" (9) means a part where the protective laminate or substrate is not adhered to the chromatography strip surface.

According to the present invention, capillary flow of a sample solution is not disturbed when a space is arranged only in a partial region of the coloring region, so the space can be arranged at least a partial region of the coloring region. However, it does not exert its effect when the partial region of the coloring region is extremely small as a matter of course, and further it becomes difficult not to paste the partial region when the partial region of the coloring region is too small.

Even if the space is the entire portion of the coloring region or becomes more wider by including the entire portion of the coloring region and its contiguous upstream and downstream regions, it will bear no problems but rather show larger effects and facilitate the pasting, so that the space is arranged generally over the entire portion of the coloring region and its upstream and downstream regions.

The upstream and downstream regions may have any extent, provided that they are not the entire portion of the chromatography strip.

The space may be arranged either on the under or top surface of the chromatography strip or on both of the top and under surfaces.

Arrangement of the space can be effected by not pasting together at least a partial region of the coloring region and the surface of the protective laminate and/or substrate which faces on said region (FIG. 1 and FIG. 2). Not to paste a partial region of the coloring region and the protective laminate and/or substrate together, a paste is not applied to the non-pasting part of the protective laminate, or, when the paste is applied, an agent capable of invalidating adhesive property of the paste is applied to the non-pasting part. All of known agents can be used as the agent capable of invalidating adhesive property of the paste.

Alternatively, in order to prevent the adhesion, a thin film (10) may be inserted between the chromatography strip and the protective laminate and/or substrate (FIG. 3). When the thin film is inserted between the protective laminate and the chromatography strip, it must be a transparent material.

Any material which does not absorb water can be used as the thin film.

As an alternative method for arranging the space, a concavity (11) is made on the surface part of the protective laminate and/or substrate which faces on at least a partial region of the coloring region (FIG. 4). The concavity can be made easily by sticking together two sheets of the protective laminate or substrate, but using only one sheet at the concavity part.

The space can also be arranged by sticking together the protective laminate and two or more of discontinued parts of the chromatography strip excluding at least a partial region of the coloring region (FIG. 5).

Also, the space can be arranged by such a manner that the protective laminate or substrate does not cover at least a partial region of the coloring region (FIG. 6).

When the space is arranged on both of the top and under surfaces of the chromatography strip, the adhering preventing method may be the same or different from one another. However, a method in which both of the protective laminate and substrate are not covered is not desirable, because it will cause damages such as bending of the chromatography strip.

The following describes the present invention further in detail with reference to the examples.

EXAMPLES

A nitrocellulose film (manufactured by Millipore, U.S.A.) of 0.5 cm×4.0 cm in size was stuck on a substrate ("pack Laminate"). By regarding the longitudinal side of the nitrocellulose film as lengthwise, a solution containing a syphilis antigen derived from *Treponema pallidum* was spotted in a line on a position about 1 cm from its bottom end and thoroughly dried to immobilize the syphilis antigen, thereby arranging a detecting region on the nitrocellulose film. In the same manner as the case of syphilis antigen, avidin was immobilized on the nitrocellulose film about 1 cm upside from the detecting region, thereby arranging a control region. A glass fiber film (manufactured by Lydall, U.S.A.) was impregnated with a labeled antigen obtained by labeling the syphilis antigen derived from *Treponema pallidum* with selenium colloid and with biotinated selenium colloid obtained by binding biotin to selenium colloid, and then the glass fiber film was dried to be used as a labeling region. The thus prepared labeling region was stuck on the substrate in such a manner that it slightly contacted with the bottom end of the previously obtained nitrocellulose film on the substrate. As a sample applying region, a non-woven fabric (manufactured by Du Pont, U.S.A.) of 0.5×1.0 cm in size was stuck on the substrate at the bottom end of the labeling region so that it contacted with the labeling region.

A protective laminate (manufactured by Lintech) is stuck on the top surface of the chromatography strip obtained in the above manner, and detection of syphilis antibody in a sample to be tested is carried out using the thus obtained chromatography strip device. A 50 μl portion of a serum sample to be tested is applied to the sample applying region of the chromatography strip device, and the result is judged 15 minutes after application of the serum by reading with the naked eye "redness" of the selenium colloid in the detecting region and control region.

The result is judged syphilis antibody positive when both of the detecting region and control region showed a red color or syphilis antibody negative when only the control region showed a red color. A case in which the control region did not become red is regarded as invalid.

In sticking the protective laminate on the chromatography strip device, the following methods were used in order to prevent the chromatography strip from adhesion to the protective laminate at the detecting region and control region on the chromatography strip.

(1) A protective laminate coated with an ink having a property to be hardened by ultraviolet ray irradiation (UV hardening ink) (manufactured by T & K TOKA) on the pasting side of the protective laminate was used. By sticking this protective laminate on the chromatography strip, a non-adhering part was provided between the protective laminate and the chromatography strip at the UV hardening ink-coated parts (detecting region and control region). The chromatography strip device obtained by this treatment will be called UV treating method.

(2) A non-adhesive part was arranged between the protective laminate and the chromatography strip by sticking a protective laminate on the chromatography strip, after coating a paste on other portions of the protective laminate than the portions where the protective laminate faces on the detecting region and control region of the chromatography strip. The chromatography strip device obtained by this method will be called partial coating method.

(3) The protective laminate was stuck on the chromatography strip excluding portions of its detecting region and control region, so that the detecting region and control region had no protective laminate. The chromatography strip device obtained by this method will be called opening method.

(4) As a control, the protective laminate was stuck on the chromatography strip in such a manner that space was not formed between the protective laminate and the chromatography strip. The chromatography strip device obtained by this method will be called conventional method.

W Using the above four chromatography strip devices, detection of syphilis antibodies in 32 samples to be tested was carried out to observe color development at the coloring regions, namely detecting region and control region. Table 1 shows the number of chromatography strip devices which showed white spots or irregular color development at these coloring regions.

TABLE 1

|  | Detecting region | | | Control region | | |
| --- | --- | --- | --- | --- | --- | --- |
|  | Lot. 1 | Lot. 2 | Lot. 3 | Lot. 1 | Lot. 2 | Lot. 3 |
| UV treating method | 0/32 | 0/32 | 0/32 | 0/32 | 0/32 | 0/32 |
| Partial coating method | 0/32 | 0/32 | 0/32 | 0/32 | 0/32 | 0/32 |
| Opening method | 0/32 | 0/32 | 0/32 | 0/32 | 0/32 | 0/32 |
| Conventional method | 7/32 | 2/32 | 11/32 | 9/32 | 13/32 | 7/32 |

EFFECTS OF THE INVENTION

As has been described in the foregoing, when a space is arranged in at least a partial region of coloring regions of the chromatography strip of the immunoassay device, capillary flow of sample solution in the chromatography strip does not become irregular in the coloring regions, so that the detection accuracy of substances to be detected is sharply improved.

Figure 1:
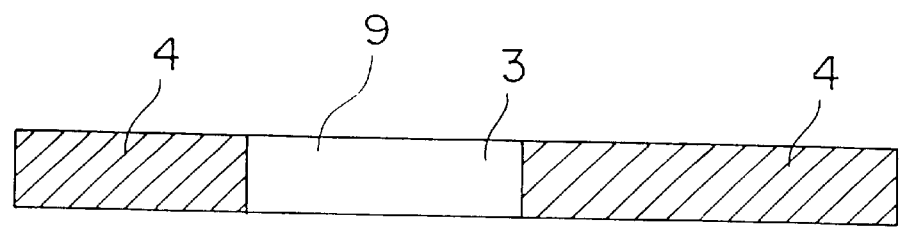
FIGS. 1A–1B illustrate an example of the immunoassay device of the present invention. In the drawing, 1A is a plan view of the pasting side of a protective laminate and 1B is a side view of the immunoassay device.
Figure 1:
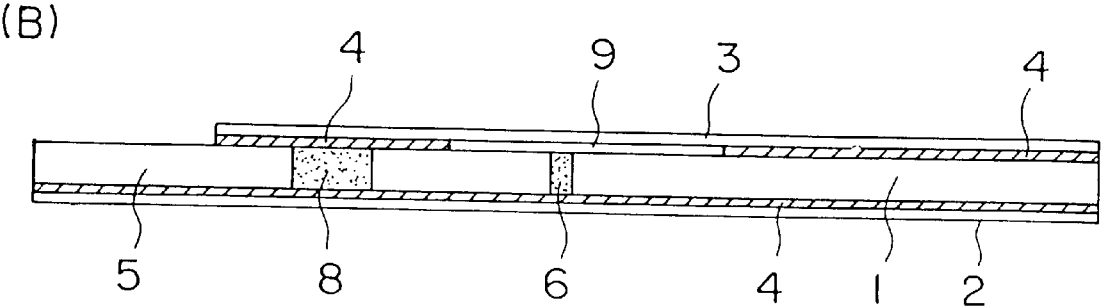
Figure 2:
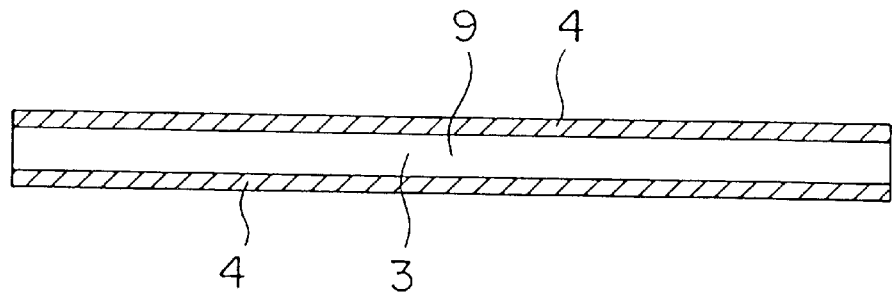
FIG. 2 is a plan view of the pasting side of a protective laminate of an example of the immunoassay device of the present invention.
Figure 3:
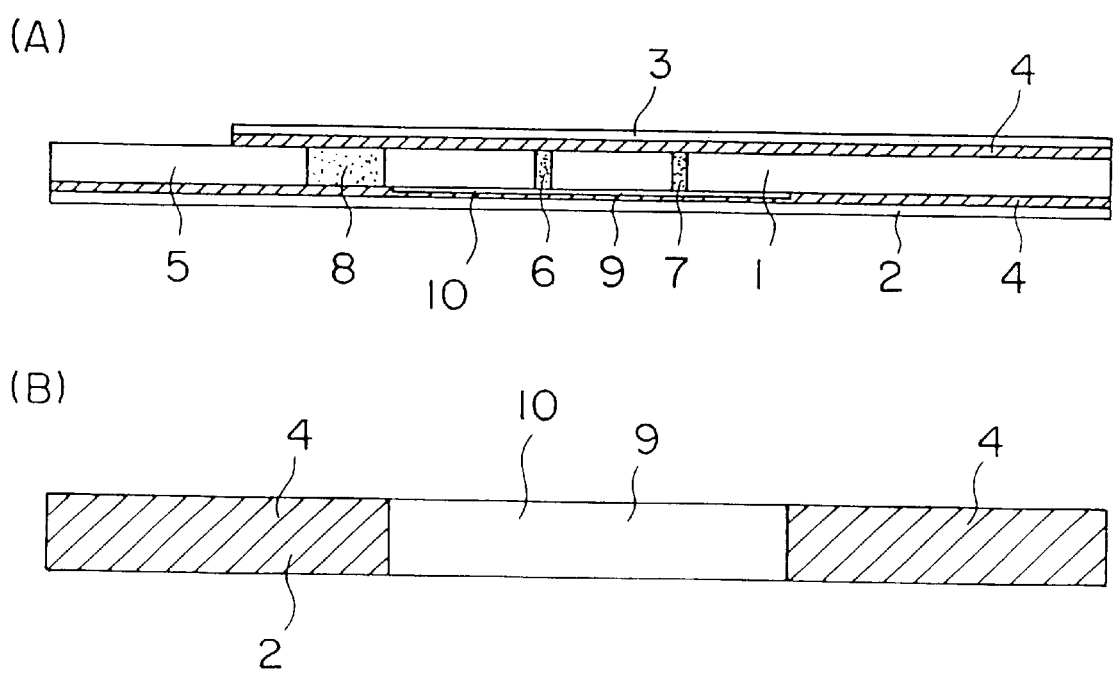
FIGS. 3A–3B illustrate an example of the immunoassay device of the present invention. In the drawing, 3A is a side view and 3B is a plan view of the pasting side of the substrate.
Figure 4:
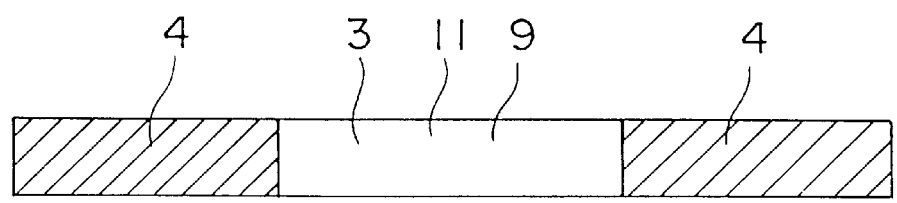
FIGS. 4A–4B illustrate an example of the immunoassay device of the present invention. In the drawing, 4A is a plan view of the pasting side of the protective laminate, and 4B is a side view of the immunoassay device.
Figure 4:
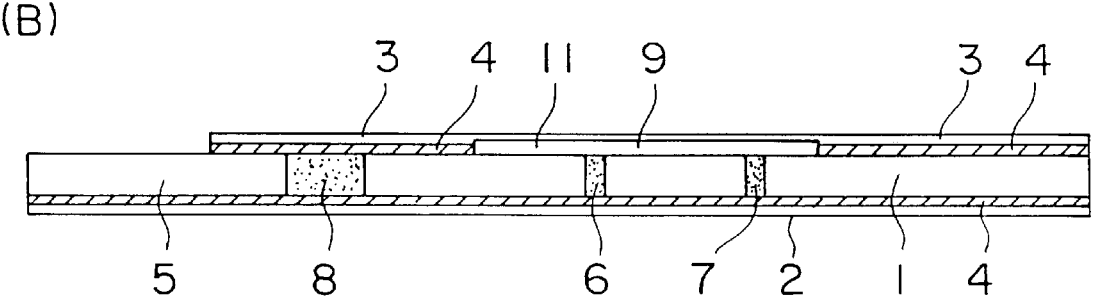
Figure 5:
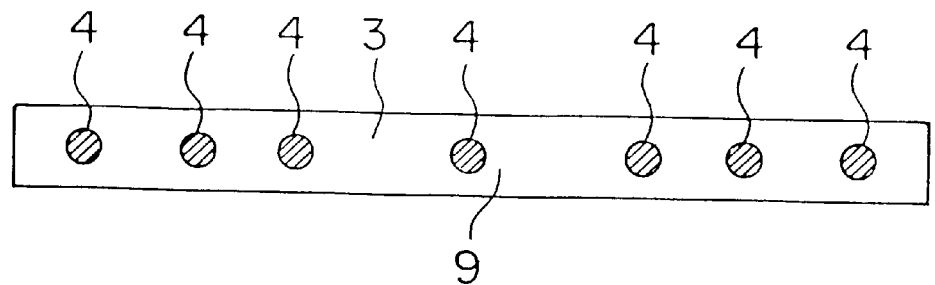
FIG. 5 is a plan view of the pasting side of a protective laminate of an example of the immunoassay device of the present invention.
Figure 6:
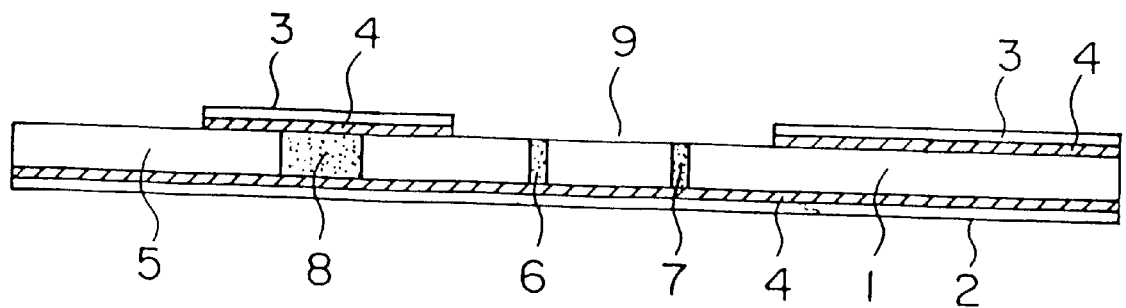
FIG. 6 is a side view of an example of the immunoassay device of the present invention.

What is claimed is:

1. A device consisting essentially of:

a chromatography strip, a substrate adhered underneath said chromatography strip, and a protective laminate adhered to the top surface of said chromatography strip, wherein a space is provided either on the top and/or under the surface of a portion of a coloring region of said chromatography strip.

2. The device according to claim 1 wherein said space is provided by preventing a portion of the coloring region from adhering to either a portion of the surface of the protective laminate or a portion of the surface of the substrate.

3. The device according to claim 2 wherein said space is provided by not applying paste to a portion of the surface of the protective laminate or a portion of the surface of the substrate.

4. The device according to claim 2 wherein said space is provided by applying an agent capable of invalidating an adhesive property of a paste to a portion of the surface of the protective laminate or a portion of the surface of the substrate.

5. The device according to claim 1, wherein said space is provided by making concave either the surface of the protective laminate or the surface of the substrate facing the coloring region.

6. The device according to claim 1, wherein said space is provided by inserting a thin film between a portion of the coloring region and either the surface of the protective laminate or the substrate.

7. The device according to claim 1, wherein the protective laminate or substrate are adhered to the chromatography strip at two or more discontinuous locations other than at the coloring region next to said space.

8. The device according to claim 1, wherein either the protective laminate or substrate does not cover the portion of the coloring region next to said space.

* * * * *